US009763858B2

(12) United States Patent
Gross et al.

(10) Patent No.: US 9,763,858 B2
(45) Date of Patent: Sep. 19, 2017

(54) SELF-HEALING DENTAL RESTORATIVE FORMULATIONS AND RELATED METHODS

(75) Inventors: Stephen M. Gross, Omaha, NE (US); Mark A. Latta, Omaha, NE (US)

(73) Assignee: Premier Dental Products Company, Plymouth Meeting, PA (US)

( * ) Notice: Subject to any disclaimer, the term of this patent is extended or adjusted under 35 U.S.C. 154(b) by 923 days.

(21) Appl. No.: 12/587,279

(22) Filed: Oct. 5, 2009

(65) Prior Publication Data

US 2011/0082232 A1    Apr. 7, 2011

(51) Int. Cl.
*A61K 6/08*     (2006.01)
*A61K 6/093*    (2006.01)
*A61K 6/083*    (2006.01)
*A61K 6/00*     (2006.01)

(52) U.S. Cl.
CPC ............. *A61K 6/093* (2013.01); *A61K 6/083* (2013.01); *A61K 6/0047* (2013.01)

(58) Field of Classification Search
CPC ................................ A61K 6/08; A61K 6/0047

USPC ......................................................... 523/115
See application file for complete search history.

(56) References Cited

U.S. PATENT DOCUMENTS

| | | | | |
|---|---|---|---|---|
| 6,830,816 | B2* | 12/2004 | Mehnert et al. | 428/423.1 |
| 6,858,659 | B2* | 2/2005 | White et al. | 523/200 |
| 7,723,405 | B2* | 5/2010 | Braun et al. | 523/212 |
| 2002/0086907 | A1* | 7/2002 | Standke et al. | 516/9 |
| 2007/0166542 | A1* | 7/2007 | Braun et al. | 428/402.21 |

* cited by examiner

*Primary Examiner* — Michael Pepitone
(74) *Attorney, Agent, or Firm* — Cozen O'Connor

(57) ABSTRACT

Dental restorative formulations comprising an additive material and a capsule incorporated into the continuous phase of a dental material. The additive material includes one or more alkoxy groups and one or more vinyl groups. The capsule includes a catalyst and a molecule with one or more silanol groups. The dental restorative formulation is applied and polymerized to form a composite. When a disturbance occurs in the dental composite, the capsule ruptures so that the catalyst initiates a condensation reaction between the molecule with one or more silanol groups and the one or more alkoxy groups thereby healing the dental composite.

10 Claims, 1 Drawing Sheet

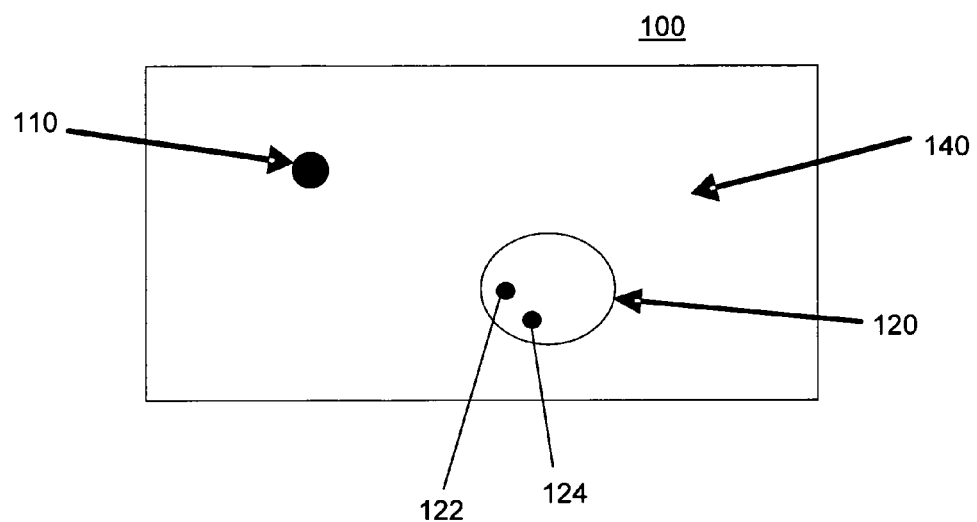

SELF-HEALING DENTAL RESTORATIVE FORMULATIONS AND RELATED METHODS

FIELD OF THE INVENTION

The present invention relates generally to self-healing composites. More specifically, the present invention relates to dental restorative formulations that are applied and polymerized to form self-healing composites with the capability to autonomically resolve disturbances occurring in the composite. The present invention also relates to methods of forming dental restorative formulations. The present invention is useful in a variety of contexts and applications in dentistry including dental repairs, restorations and reconstructions.

BACKGROUND OF THE INVENTION

For purposes of this application, the present invention is discussed in reference to dental applications, but the discussion with respect to dental repair, regeneration or reconstruction is merely exemplary. The present invention is applicable to any context and application that may require self-healing composites.

Dental composites have improved over time. One of the first known dental composites was made with silicate cement. A problem with silicate cement was that it required extreme accuracy during preparation to ensure such a restorative would remain as long as possible. Poorly-made silicate cement restoratives could get destroyed even under the influence of saliva. Another problem with silicate cement was discoloration. Silicate cement absorbs food dyes and tends to yellow over time.

Silicate cement was soon replaced by dental acrylic plastics. Dental acrylic plastics often led to multiple complications, such as pulpitis and periodontitis. Pulpitis is tooth decay that penetrates through the enamel and dentin to reach the pulp of a tooth and periodontitis is any number of inflammatory diseases that affect the tissues surrounding and supporting a tooth. Additionally, acrylic plastics were difficult to polish. Amalgams were an improvement over dental acrylic plastics, but have been shunned by many because of their mercury content.

Metal-based amalgams, then porcelain or other ceramic materials, were used in a variety of remedial dental procedures. Synthetic composites are used as practical alternatives to these materials for such procedures. Synthetic composites typically include a resin with at least one additive to impart a desired property. The composite generally starts out as a paste or liquid and begins to harden when it is activated, either by adding a catalyst, adding water or another solvent, or photoactivation. Advantageously, synthetic composites provide an aesthetically more natural appearance versus porcelain or other ceramic materials.

Synthetic composites are typically made from complex mixtures of multiple components. Synthetic composites must be completely dissolvable in a fluid vehicle, yet remain flowable and viscous; undergo minimal thermal expansion during polymerization; be biocompatible with surrounding surfaces of tooth enamel and colloidal dentin; and, have aesthetic similarity to natural dentition in terms of color tone and polishable texture. Furthermore, synthetic composites must have sufficient mechanical strength and elasticity to withstand ordinary compressive occlusive forces, without abnormal wearing and without causing abrasion to dentinal surfaces.

The different varieties of synthetic composites may be approximately divided into three main groups of products: synthetic resin-based dental composites, glass-based dental composites, and hybrid dental composites.

A synthetic resin-based composite typically comprises materials such as silicate glass or processed ceramic that provides an essential durability to the composite. A synthetic resin-based dental composite typically comprises several monomers combined together. A monomer is a chemical that can be bound as part of a polymer. The synthetic resin-based dental composite includes other materials, such as silicate glass or processed ceramic that provides an essential durability to the composite. These materials may also be made from an inorganic material, consisting of a single type or mixed variety of particulate glass, quartz, or fused silica particles. Using differing types of inorganic materials, with differing diameter sizes or size mixtures, results in differing material characteristics.

Glass-based dental composites are made from glass particles, such as powdered fluoroaluminosilicate, dissolved in an aqueous polyalkenoate acid. An acid/base reaction occurs spontaneously, causing precipitation of a metallic polyalkenoate, which subsequently solidifies gradually. The glass particles may be made from silicate, such as silicone dioxide or aluminum silicate, but may also include an intermixture of barium, borosilicate, alumina, aluminum/calcium, sodium fluoride, zirconium, or other inorganic compounds. Some of the earlier glass-based composites were formulated to contain primarily a mixture of acrylic acid and itaconic acid co-monomers. However, more recently such hybrid products are modified to include other polymerizable components, such as hydroxyethyl methacrylate ("HEMA") or 2,2-bis[4-(2-hydroxy-3-methacryloyloxypropoxy) phenyl]propane ("Bis-GMA").

Hybrid composites are the third category of synthetic composites. Similar to glass-based composites, hybrid composites are typically made from a combination of inorganic compounds and organic compounds, for example, glass particles with one or more polymers. Hybrid composites may comprise water-soluble polymers other than polyalkenoate, such as HEMA and other co-polymerizing methacrylate-modified polycarboxylic acids, which are catalyzed by photoactivation. Other hybrid dental composites may be modified to include polymerizable tertiary amines, catalyzed by reaction with peroxides.

Synthetic dental composites are increasingly used more often for dental procedures, such as restoration, reconstruction and repair, for example, fillings, crowns, bridges, dentures, orthodontic appliances, retainers, cements, posts and ancillary parts for dental implants to name a few. Most common, synthetic dental composites are used for anterior Class III and Class V reconstructions, for smaller size Class I and Class II molar reconstructions, for color-matching of cosmetic veneers, and for cementing of crowns and overlays. Nonetheless certain disadvantages of these materials have been noted. For example, the trace amounts of unconverted monomers and/or catalyst that may remain within the composite and, if subsequently absorbed systemically in humans, may be potentially physiologically harmful.

Most common, dental composites are used for reconstructions, color-matching, and cementing of crowns and overlays. Nonetheless, dental composites maintain certain disadvantages. For example, these composites tend to wear more rapidly. Perhaps the most significant disadvantage associated with dental composites is that they have a low resistance to disturbances such as cracks, breaks, fractures, splits, fissures, and gaps to name a few. Even relatively minor surface disturbances within the composite may progressively widen and expand, eventually resulting in partial or complete damage of the dental composite.

This low resistance to disturbances is also correlated with the proportional volume of the amount of synthetic composite required, or the lesser fraction of intact enamel and dentinal tooth material that remains available, prior to reconstruction, restoration or repair. It is well established from studies of the "cracked tooth syndrome" that once a damaging fracture has occurred, tooth loss may be almost inevitable, especially for carious teeth that have been previously filled. An improved synthetic dental composite having greater resistance to fracture would be significantly advantageous.

Synthetic composites having self-healing characteristics are known in the art, as illustrated for example in U.S. Pat. Nos. 6,518,330 and 6,858,659, describing self-repair of a polyester material containing unreacted amounts of dicyclopentadiene ("DCPD") monomer stored within a polyester matrix resin, as sequestered within polyoxymethyleneurea ("PMU") microcapsules. From a fracturing mechanical stress sufficient to cause rupturing of one or more microcapsule, the monomer is reactively released. As the monomer contacts the polyester matrix, a polymerization occurs. The in situ polymerization occurs as a result of a ruthenium-based Grubbs catalyst or Schrock catalyst, which may be incorporated into the matrix. Alternatively, the catalyst may be stored within a fraction of separately prepared microcapsules, or may be contained within the same material comprising the microcapsule outer wall.

Although a composite having self-healing characteristics is known in the art, there is still a demand for improved dental restorative formulations having self-healing characteristics, or the ability to automatically correct any disturbances, occurring in the composite as well as methods of making such restorative formulations. The present invention satisfies this demand.

SUMMARY OF THE INVENTION

The present invention is directed to dental restorative formulations having self-healing characteristics as a composite, and methods of making such restorative formulations.

Dental composites are formed from the polymerization of a restorative formulation. Typically, a restorative formulation comprises a resin matrix or dental material, a filler material such as silica, an initiator to begin the polymerization reaction of the dental materials when external energy such as light or heat is applied to the formulation and a catalyst to control polymerization speed. When a restorative formulation is applied, for example directly to a tooth, external energy is applied to polymerize the restorative formulation forming a composite.

A problem with dental composites is that they may be susceptible to disturbances. Disturbances include, for example, cracks, discontinuities, breaks, fractures, splits, fissures, and gaps to name a few.

The present invention solves the problem of disturbances occurring in composites by incorporating additives in dental restorative formulations to provide "self-healing" characteristics. Therefore, when disturbances occur in a composite, the composite repairs, regenerates, or reconstructs itself such that the function, integrity and morphology of the composite is brought back to an original or almost original condition.

Dental composites can be used to repair, regenerate or reconstruct a variety of dental structures such as fillings, crowns, bridges, dentures, orthodontic appliances, retainers, cements, posts and ancillary parts for dental implants. The present invention contemplates dental restorative formulations that include functional groups that take part in a chemical reaction to result in self-healing composites.

The present invention includes dental restorative formulations comprising a resin matrix or dental material with a continuous phase, wherein the dental material includes an additive material and a capsule. The additive material and capsule are stored in the continuous phase of the dental material. The dental material is one or more monomers as discussed below.

For purposes of this application, a resin matrix or dental material used for dental restorative formulations may include any combination of one or more monomers. Monomers include synthetic monomers and natural monomers. Synthetic monomers include acrylic monomers as well as hydrocarbons such as ethene as well as acrylic acid, methyl methacrylate, styrene, and acrylamide. Natural monomers include, for example, amino acids and glucose.

Dental materials according to the present invention may include one or more selected from the group of: 2,2-bis[4-(2-hydroxy-3-methacryloyloxypropoxy) phenyl]propane ("Bis-GMA"), dimethacryloxyethyl 2,2,4-trimethylhexamethylene diurethane ("UDMA"), and 1,6-bis-[2-methacryloxy-ethoxycarbonylamino]-2,2,4-trimethylhexane ("UEDMA"), triethyleneglycol dimethacrylate ("TEGDMA"), polyethylene glycol dimethacrylate ("PEGDMA"), glyceroldimethacrylate ("GDM"), methacryloyloxyethyl maleate ("MEMA"), diethyleneglycol dimethacrylate ("DEGDMA"), hexanediol dimethacrylate ("HDMA"), hexanediol diacrylate ("HDDA"), trimethylolpropanetriacrylate ("TMPTA"), trimethylolpropanetrimethacrylate ("TMPTMA"), ethoxylated trimethylolpropanetriacrylate ("EOTMPTA"), hydroxyethyl methacrylate ("HEMA") and ethoxylated bisphenol A dimethacrylate ("EBPADMA"), isopropyl methacrylate; n-hexyl acrylate; stearyl acrylate; diallyl phthalate; divinyl succinate; divinyl adipate; divinyl phthalate; allyl acrylate; glycerol triacrylate; ethyleneglycol diacrylate; 1,3-propanediol di(meth)acrylate; decanediol dimethacrylate; 1,12-dodecanediol di(meth) acrylate; trimethylolpropane mono- or di-(meth)acrylate; trimethylolpropane triacrylate; butanediol di(meth)acrylate; 1,2,4-butanetriol trimethacrylate; 1,4-cyclohexanediol diacrylate; pentaerythritol tetra(meth)acrylate; sorbitol mono-, di-, tri-, tetra-, or penta-(meth)acrylate; sorbitol hexa-(meth) acrylate; tetrahydrofurfuiryl (meth)acrylate; bis[1-(2-acryloxy)]-p-ethoxyphenyldimethylmethane; bis[1-(3-acryloxy-2-hydroxy)]-p-propoxyphenyldimethylmethane; 2,2,4-trimethylhexamethylene diisocyanate; tris-hydroxyethylisocyanurate trimethacrylate, glycerol phosphate monomethacrylates; glycerol phosphate dimethacrylates; hydroxyethyl methacrylate phosphates; 2-hydroxypropyl (meth)acrylate; citric acid di- or tri-methacrylates; fluoropolymer-functional (meth)acrylates; poly(meth)acrylated polymaleic acid; poly(meth)acrylated polycarboxyl-polyphosphonic acid; poly(meth)acrylated polychlorophosphoric acid; poly(meth)acrylated polysulfonic acid; poly (meth)acrylated polyboric acid; polymerizable bisphosphonic acids, and siloxane-functional (meth)acrylate polysiloxanes, defined as products resulting from hydrolytic polycondensation of one or more of the following silanes: bis[2-(2-(methacryloyl oxyethoxycarbonyl)ethyl)]-3-¬ tri-ethoxysily-lpropyl amine, bis[2-(2(1)-(methacryloyloxy-propoxycarbonyl)ethyl)]-3-triet-hoxysilylpropyl amine, 1,3 (2)-dimethacryloyloxypropyl-[3-(3-triethoxysilyl-propyl) aminocarbonyl]propionate, 1,3(2)- dimethacryloyloxypropyl-[4-(3-trie-thoxysilyl propyl) aminocarbonyl]butyrate, 1,3(2)-dimethacryloyloxypropyl-[-4-(3-triethoxysilylpropyl)-N-¬ethylaminocarbonyl] butyrate, 3-[1,3(2)-dimethacryloyl oxypropyl)-2(3)-oxycarbonylamido]¬propyltriethoxysilane, glycerol phosphate monomethacrylates, glycerol phosphate dimethacrylates, hydroxyethyl methacrylate phosphates, citric acid di- or tri-methacrylates, poly(meth)acrylated oligomaleic acid, poly(meth)acrylated polymaleic acid, poly(meth)acrylated poly(meth)acrylic acid, poly(meth)acrylated polycarboxyl-polyphosphonic acid, poly(meth)acrylated polychlorophosphoric acid, poly(meth)acrylated polysulfonic acid, poly(meth)acrylated polyboric acid and polymerizable bisphosphonic acids. It is contemplated that any formulation for a dental composite may include multiple monomers, including any combination of the foregoing.

The additive material is a monomer that includes one or more alkoxy groups and one or more vinyl groups, for example, monomeric, oligomeric or polymeric vinylalkoxysiloxanes or vinylethoxysiloxanes. In one embodiment, it is contemplated that the additive material accounts for 1-15 wt % of the dental restorative formulation.

The dental restorative formulation further includes a capsule comprising a catalyst and a molecule with one or more silanol groups. In one embodiment, it is contemplated that the capsule accounts for about 1-15 wt % of the dental restorative formulation.

The catalyst is selected from the group comprising of organotin catalysts including stannous octooate, dialkyl dicarboxylate or dibutyl tin dilaurate, and platinum compounds including chloroplatinic acid and hydride-functional siloxanes. In one embodiment, the catalyst is tin (II) ethylhexanoate.

Methods for constructing capsules or microspheres may by physical or chemical. Physical methods of manufacturing include pan coating, air-suspension coating, centrifugal extrusion, vibrational nozzle and spray-drying. Chemical methods of manufacturing include polymerization such as interfacial polymerization, in-situ polymerization and matrix polymerization. In interfacial polymerization, at least two monomers are dissolved separately in immiscible liquids. Upon interface between the liquids, rapid reaction occurs creating a thin shell or wall of the microsphere. In-situ polymerization is the direct polymerization of a single monomer carried out on the particle surface. Matrix polymerization, a core material is imbedded during formation of the microsphere. Capsules might also be constructed by using sol-gel techniques, by aqueous or organic solution precipitation synthesis methods, complex coacervation, interfacial polymerization, or by other methods known in the art.

As mentioned above, when a disturbance occurs in the dental composite, the capsule ruptures so that the catalyst initiates a condensation reaction between the molecule with one or more silanol groups and the molecule with one or more alkoxy groups thereby healing the dental composite.

A primary object of the present invention is to provide dental restorative formulations with self-healing characteristics, or capability to autonomically resolve disturbances, occurring in composites polymerized from the restorative formulations.

Another object of the present invention is to provide a dental restorative formulation that polymerizes to a composite that wears slowly compared to existing composites and has a greater resistance to disturbances.

Another object of the present invention is to provide a dental restorative formulation that can be applied as a monomer directly to the teeth of the patient.

Another object of the present invention is to provide a dental restorative formulation that is biocompatible.

It will of course be understood that the aspects and objectives of the invention are various, and need not be all present in any given embodiment of the invention. The features, advantages and accomplishments of the invention will be further appreciated and understood upon consideration of the following detailed description of embodiments of the invention.

BRIEF DESCRIPTION OF THE DRAWINGS

FIG. 1 illustrates an embodiment of a dental restorative formulation according to the present invention.

DETAILED DESCRIPTION

This application incorporates by reference the entire subject matter of U.S. patent application Ser. No. 11/809,248, filed May 31, 2007.

As shown in FIG. 1, a dental restorative formulation 100 includes an additive material 110 and a capsule 120 incorporated into the continuous phase of a dental material 140. The dental material 140 includes one or more monomers selected from the group comprising of: 2,2-bis[4-(2-hydroxy-3-methacryloyloxypropoxy) phenyl]propane ("BisGMA"), dimethacryloxyethyl 2,2,4-trimethylhexamethylene diurethane ("UDMA"), and 1,6-bis-[2-methacryloxyethoxycarbonylamino]-2,2,4-trimethylhexane ("UEDMA"), triethyleneglycol dimethacrylate ("TEGDMA"), polyethylene glycol dimethacrylate ("PEGDMA"), glyceroldimethacrylate ("GDM"), methacryloyloxyethyl maleate ("MEMA"), diethyleneglycol dimethacrylate ("DEGDMA"), hexanediol dimethacrylate ("HDMA"), hexanediol diacrylate ("HDDA"), trimethylolpropanetriacrylate ("TMPTA"), trimethylolpropanetrimethacrylate ("TMPTMA"), ethoxylated trimethylolpropanetriacrylate ("EOTMPTA"), hydroxyethyl methacrylate ("HEMA") and ethoxylated bisphenol A dimethacrylate ("EBPADMA"), isopropyl methacrylate; n-hexyl acrylate; stearyl acrylate; diallyl phthalate; divinyl succinate; divinyl adipate; divinyl phthalate; allyl acrylate; glycerol triacrylate; ethyleneglycol diacrylate; 1,3-propanediol di(meth)acrylate; decanediol dimethacrylate; 1,12-dodecanediol di(meth)acrylate; trimethylolpropane mono- or di-(meth)acrylate; trimethylolpropane triacrylate; butanediol di(meth)acrylate; 1,2,4-butanetriol trimethacrylate; 1,4-cyclohexanediol diacrylate; pentaerythritol tetra(meth)acrylate; sorbitol mono-, di-, tri-, tetra-, or penta-(meth)acrylate; sorbitol hexa-(meth)acrylate; tetrahydrofurfuiryl (meth)acrylate; bis[1-(2-acryloxy)]-p-ethoxyphenyldimethylmethane; bis[1-(3-acryloxy-2-hydroxy)]-p-propoxyphenyldimethylmethane; 2,2,4-trimethylhexamethylene diisocyanate; tris-hydroxyethylisocyanurate trimethacrylate, glycerol phosphate monomethacrylates; glycerol phosphate dimethacrylates; hydroxyethyl methacrylate phosphates; 2-hydroxypropyl (meth)acrylate; citric acid di- or tri-methacrylates; fluoropolymer-functional (meth)acrylates; poly(meth)acrylated polymaleic acid; poly(meth)acrylated polycarboxyl-polyphosphonic acid; poly(meth)acrylated polychlorophosphoric acid; poly(meth)acrylated polysulfonic acid; poly (meth)acrylated polyboric acid; polymerizable bisphosphonic acids, and siloxane-functional (meth)acrylate polysiloxanes, defined as products resulting from hydrolytic polycondensation of one or more of the following silanes: bis[2-(2-(methacryloyl oxyethoxycarbonyl)ethyl)]-3-¬triethoxysily-lpropyl amine, bis[2-(2(1)-(methacryloyloxypropoxycarbonyl)ethyl)]-3-triet-hoxysilylpropyl amine, 1,3 (2)-dimethacryloyloxypropyl-[3-(3-triethoxysilyl-propyl) aminocarbonyl]propionate, 1,3(2)-dimethacryloyloxypropyl-[-4-(3-trie-thoxysilyl propyl) aminocarbonyl]butyrate, 1,3(2)-dimethacryloyloxypropyl-[-4-(3-triethoxysilylpropyl)-N-¬ethylaminocarbonyl] butyrate, 3-[1,3(2)-dimethacryloyl oxypropyl)-2(3)-oxycarbonylamido]¬propyltriethoxysilane, glycerol phosphate monomethacrylates, glycerol phosphate dimethacrylates, hydroxyethyl methacrylate phosphates, citric acid di- or tri-methacrylates, poly(meth)acrylated oligomaleic acid, poly(meth)acrylated polymaleic acid, poly(meth)acrylated poly(meth)acrylic acid, poly(meth)acrylated polycarboxyl-polyphosphonic acid, poly(meth)acrylated polychlorophosphoric acid, poly(meth)acrylated polysulfonic acid, poly(meth)acrylated polyboric acid and polymerizable bisphosphonic acids. In one embodiment, the dental material may be a formulation for a resin modified glass ionomer cement.

The additive material 110 includes one or more alkoxy groups and one or more vinyl groups. In one embodiment, the additive material 110 is monomeric, oligomeric or polymeric vinylalkoxysiloxanes or vinylethoxysiloxanes. In one embodiment, it is contemplated that the additive material 110 accounts for 1-15 wt % of the dental restorative formulation 100.

The dental restorative formulation 100 further includes a capsule 120 comprising a catalyst 122 and a molecule 124 with one or more silanol groups. In one embodiment, it is contemplated that the capsule 120 accounts for about 1-15 wt % of the dental restorative formulation 100.

The catalyst 122 is selected from the group comprising of organotin catalysts including stannous octooate, dialkyl dicarboxylate or dibutyl tin dilaurate, and platinum compounds including chloroplatinic acid and hydride-functional siloxanes. In one embodiment, the catalyst is tin (II) ethylhexanoate.

The dental restorative formulation 100 is applied and polymerized to form a composite. When a disturbance occurs in the dental composite, the capsule 120 ruptures releasing the contents of the capsule 120. For example, the catalyst 122 specifically tin (II) ethylhexanoate, of the capsule 120 is released to initiate a condensation reaction between the molecule 124 with one or more silanol groups and the one or more alkoxy groups of additive material 110, thereby healing the dental composite.

Those of ordinary skill in the art will appreciate that the various derivates of dental materials, functional groups, and catalysts discussed herein can be utilized with embodiments in accordance with the present invention. The invention has been described with reference to a certain described embodiment. Obviously, modifications and alterations will occur to others upon reading and understanding the preceding detailed description. Indeed, it is contemplated that functional groups and catalysts for use in accordance with the present invention could preferably be substituted in a number of ways. It is intended that the invention be construed as including all such modifications and alterations insofar as they come within the scope of the appended claims or the equivalents thereof.

What is claimed is:

1. A dental restorative formulation, comprising:
    a dental material and a continuous phase of said dental material,
    wherein said dental material includes a precursor matrix comprising one or more di-acrylate monomers selected from the group consisting of 2,2-bis[4-(2-hydroxy-3-methacryloyloxypropoxy) phenyl]propane ("Bis-GMA"), dimethacryloxyethyl 2,2,4-trimethylhexamethylene diurethane ("UDMA"), triethyleneglycol dimethacrylate ("TEGDMA"), and combinations thereof, and an additive material; and wherein said dental material includes a filler comprising a capsule, wherein said additive material includes one or more alkoxy groups and one or more vinyl groups, and the capsule comprising a catalyst and a molecule, wherein said molecule includes one or more silanol groups, wherein,
    the dental restorative formulation is polymerized with the di-acrylate monomers wherein the vinyl group reacts with the dental monomer in the precursor matrix to form the continuous phase of a composite and upon the occurrence of a disturbance in the composite said capsule ruptures such that said catalyst initiates a condensation reaction to polymerize said additive material wherein one or more silanol groups of said molecule is reactive with one or more of said alkoxy functional group of said additive material to form silyl ether linkages, thereby healing the dental composite.

2. The dental restorative formulation of claim 1, wherein said additive material is vinylethoxysiloxane.

3. The dental restorative formulation of claim 2, wherein said vinylethoxysiloxane is oligomeric.

4. The dental restorative formulation of claim 2, wherein said vinylethoxysiloxane is polymeric.

5. The dental restorative formulation of claim 2, wherein said vinylethoxysiloxane is monomeric.

6. The dental restorative formulation of claim 1, wherein said catalyst is tin (II) ethylhexanoate.

7. The dental restorative formulation of claim 1, wherein said capsule accounts for about 1-15 wt % of the dental restorative formulation.

8. The dental restorative formulation of claim 1, wherein said additive material accounts for 1-15 wt % of the dental restorative formulation.

9. The dental restorative formulation of claim 1, wherein said catalyst includes at least one of organotin catalysts including at least one of stannous octooate, dialkyl dicarboxylate or dibutyl tin dilaurate, and platinum compounds including at least one of chloroplatinic acid or hydride-functional siloxanes.

10. A method of forming a dental composite, comprising the steps of:
    combining a dental material including a precursor matrix comprising one or more di-acrylate monomers selected from the group consisting of Bis-GMA, UDMA, TEGDMA, or combinations thereof and a continuous phase of said dental material including an additive material and a capsule, wherein the additive material includes one or more alkoxy groups and one or more vinyl groups, and the capsule comprising a catalyst and a molecule including one or more silanol groups to form a dental restorative formulation;
    applying the dental restorative formulation to at least one of a tooth or dental structure;
    polymerizing the di-acrylate monomers in the dental restorative formulation to form a dental composite; and
    wherein rupture of the capsule results in the catalyst initiating a condensation reaction between the molecule and the additive material whereby forming silyl ether linkages to heal the dental composite.

* * * * *